United States Patent [19]

Hammer

[11] Patent Number: 5,316,627
[45] Date of Patent: May 31, 1994

[54] PROCESS FOR PRODUCING ODORLESS DIMETHYL ETHER

[75] Inventor: Hartmut Hammer, Cologne, Fed. Rep. of Germany

[73] Assignee: RWE-DEA Aktiengesellschaft fuer Mineraloel und Chemie, Fed. Rep. of Germany

[21] Appl. No.: 955,083

[22] Filed: Oct. 1, 1992

[30] Foreign Application Priority Data

Oct. 4, 1991 [DE] Fed. Rep. of Germany ....... 4132993

[51] Int. Cl.$^5$ ............... B01D 3/14; B01D 15/04; C07C 41/42
[52] U.S. Cl. ........................... 203/34; 203/38; 203/41; 203/DIG. 19; 568/698; 568/699
[58] Field of Search ............... 203/34, 35, 29, 38, 203/41, DIG. 19, DIG. 6; 568/697–699, 917

[56] References Cited

U.S. PATENT DOCUMENTS

| | | | |
|---|---|---|---|
| 2,792,344 | 5/1957 | Tidwell | 568/917 |
| 3,021,374 | 2/1962 | Radzitsky | 568/917 |
| 3,433,841 | 3/1969 | Dehn et al. | 568/917 |
| 4,453,020 | 6/1984 | Klinkman et al. | 568/917 |
| 4,560,807 | 12/1985 | Murai et al. | 568/698 |
| 4,802,956 | 2/1989 | Dornhagen et al. | 568/698 |
| 5,037,511 | 8/1991 | Dornhagen et al. | 568/698 |

FOREIGN PATENT DOCUMENTS 407038 1/1991 European Pat. Off. ............ 568/698

Primary Examiner—Wilbur Bascomb, Jr.
Attorney, Agent, or Firm—Thomas H. Whaley

[57] ABSTRACT

This invention relates to a process for producing odourless dimethyl ether (DME) which is thus an excellent propellant. This dimethyl ether is produced from methanol, the methanol feed, prior to the reaction to form dimethyl ether, and/or the dimethyl ether product still containing odorants being treated with acidic materials, preferably acidic ion exchangers.

5 Claims, 2 Drawing Sheets

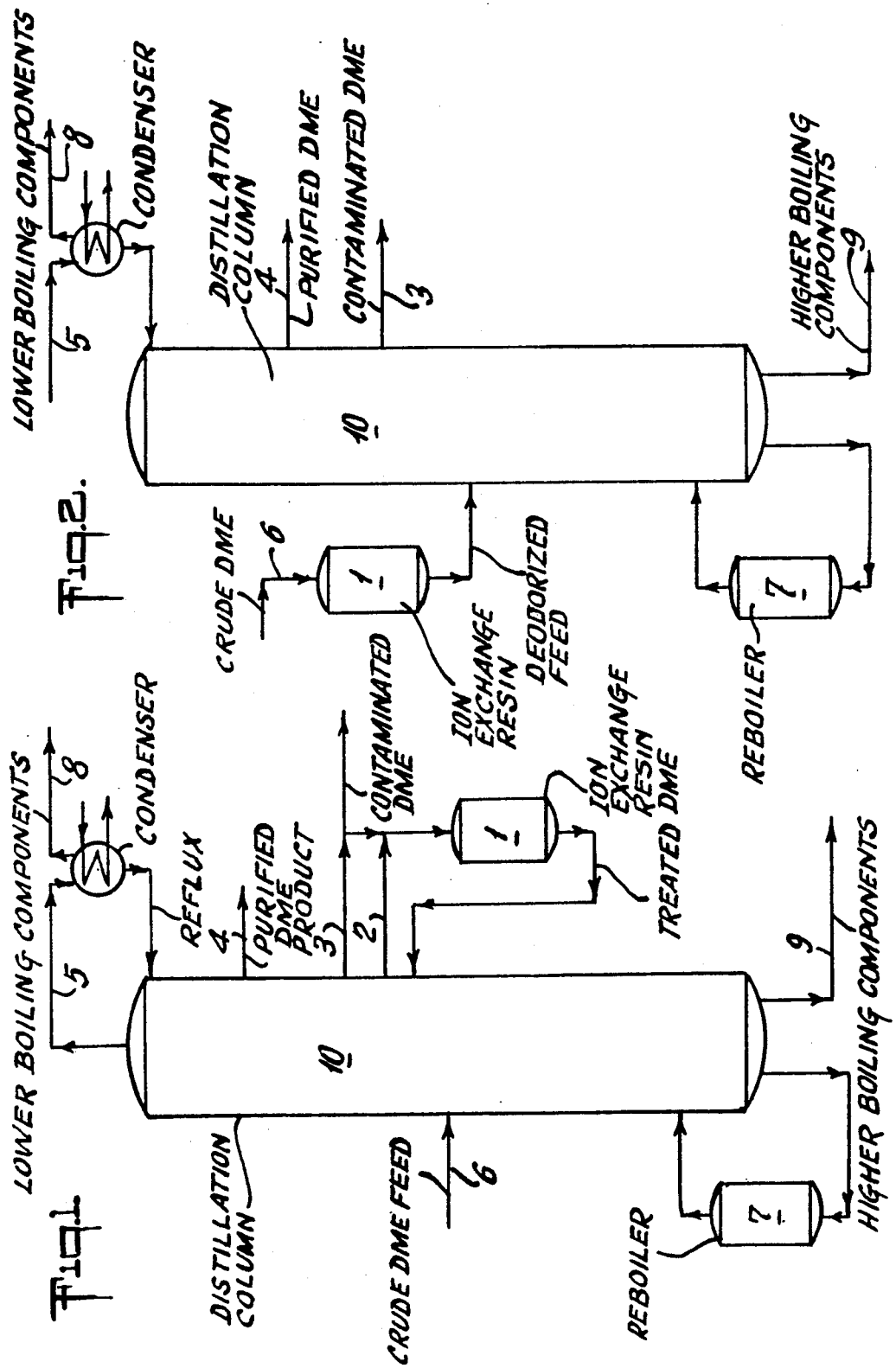

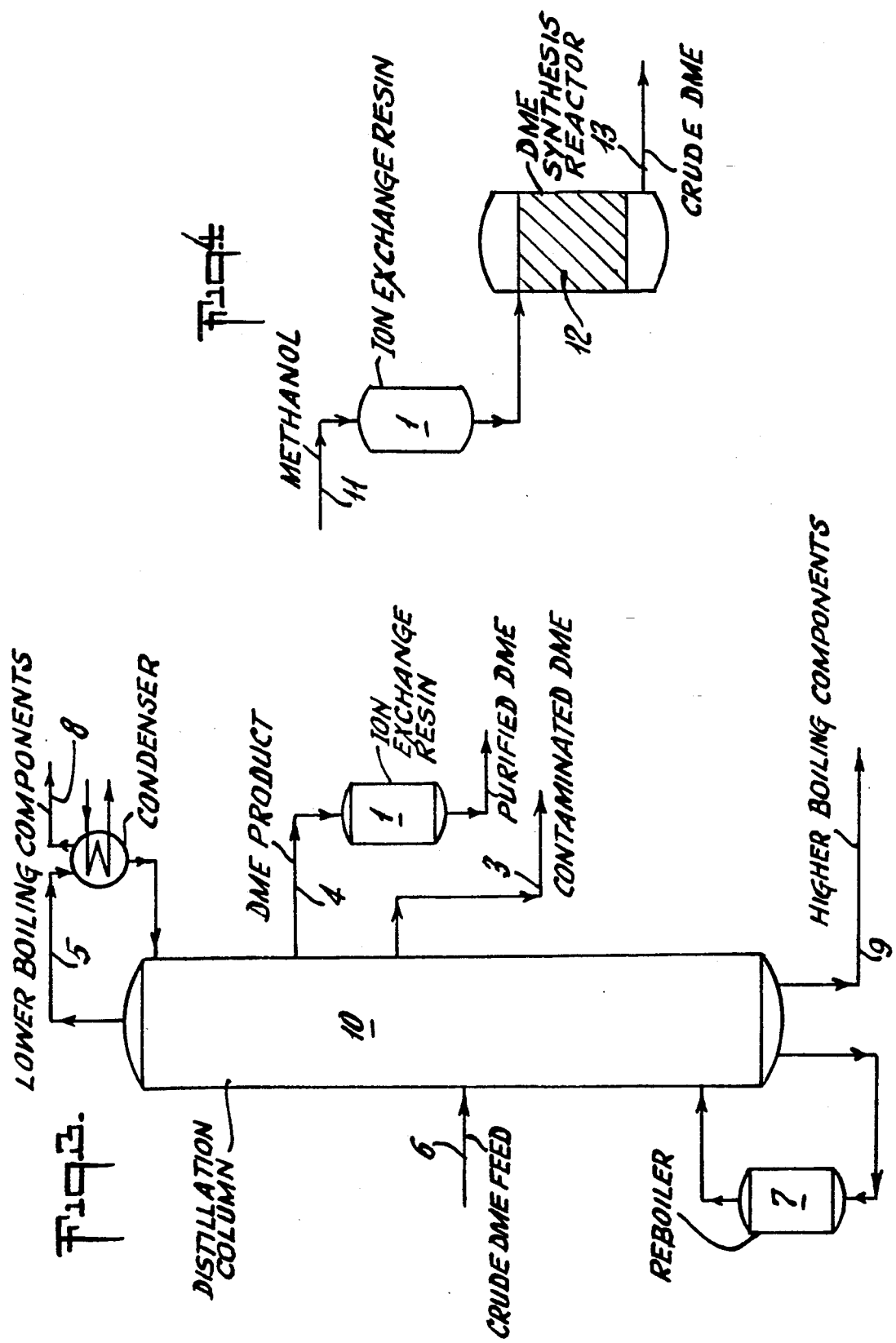

PROCESS FOR PRODUCING ODORLESS DIMETHYL ETHER

This invention relates to a process for improving the odour of dimethyl ether (DME) produced from methanol, particularly to a process for producing odourless dimethyl ether by dehydration of methanol and subsequent purifying distillation of the crude dimethyl ether.

It is generally known that the chlorofluorocarbons (CFCs) used so far as aerosol propellants have an ozone-depleting effect in the stratosphere. Due to their chemical stability CFCs have sufficiently long lives allowing them to penetrate into this region where, under the influence of sun light, they react with the ozone, thus destroying the ozone shield which is of vital importance for reducing ultraviolet radiation.

Dimethyl ether does not cause such damage. The ether is soluble in water and photochemically relatively reactive such that it is destroyed by reactions taking place in the troposphere, i.e. before reaching the ozone layer.

It is known that spray cans contain an active substance, such as a deodorant, perfume, insecticide, paint, plus a solvent, mostly ethanol, and a propellant. As a result of its polarity dimethyl ether can also be used in combination with water or water-alcohol mixtures as solvents because dimethyl ether is soluble in water. On the other hand, the dimethyl ether itself may serve as a propellant if nonpolar solvents, e.g. hydrocarbons, are used. In either case homogeneous mixtures are obtained so that early escape of the propellant from the can is prevented and complete withdrawal of the active substance dissolved in the solvent is guranteed. Accordingly, dimethyl ether has excellent properties as a propellant and, consequently, has been of increasing use in spraying applications.

A prerequisite for using dimethyl ether as a propellant, especially in household and cosmetic applications, is that it is free from any undesirable odor.

Dimethyl ether is produced by dehydration of pure methanol. Pure methanol contains as much as 99.9 weight percent methanol but also lots of impurities in ppm quantities. Further odorous impurities are formed during the reaction of methanol.

Typical impurities are dimethylamine (b.p. 6.9° C.), dimethylsulphide (b.p. 37.3° C.), methylmercaptane (b.p. 5.8° C.), formaldehyde (b.p. −21° C.), formaldehyde dimethylacetal (b.p. 45.5° C.), trimethylamine, compounds of mono- and dimethylamine with formaldehyde, formic acid, formic acid amides, methyl formate (b.p. 31.5° C.), acetic acid, acetic acid amides, methyl acetate (b.p. 56.95° C.), hydrocarbons and other trace odorants.

Since the boiling points of part of the impurities are close together and as the impurities form a number of azeotropic mixtures, it is very difficult to eliminate them by distillation since only trace quantities are present.

The methanol is dehydrated by heterogeneous catalysis, preferably at a temperature in the range of between about 250° C. and 400° C. and at a pressure of between about 8 and 15 bar. Suitable catalysts are $Al_2O_3$, $SiO_2$, aluminium silicate and, preferably, $\gamma$-alumina. The reaction mixture mainly composed of methanol, water and dimethyl ether is purified by distillation, see for instance patent specification DD-270 901 A1.

In recent years several processes for producing largely odourless dimethyl ether have been described. For instance, EP 0 124 078-A describes a process wherein DME is withdrawn as a lateral stream from the first pressurized column, while those impurities boiling between DME and methanol are removed overhead from the second column operated at a lower pressure than the first. Methanol is withdrawn as a lateral stream from the second column. Although by said process, unlike processes of the prior art, higher-purity DME is obtained, both distillation columns must be equipped with a great number of plates involving not only high investment but also high operating cost. Furthermore, there is the risk that not all of the impurities boiling between DME and methanol will reach the second column, but that they may accumulate instead in the first column and will then be withdrawn with the DME resulting in an undesirable odor of the product.

European patent application 0 270 852-A2 describes a process for producing DME from methanol in the presence of a $\gamma$-$Al_2O_3$ catalyst containing very little $SiO_2$. A high-purity, largely odourless DME then is obtained by purifying distillation whereby those impurities boiling between DME and methanol are removed as a lateral stream from certain plates of a single column. A further improvement of said process has been disclosed in European patent application EP-0 340 324-A2.

Under troublefree, optimal conditions any of said processes will allow one to produce dimethyl ether which is suitable as a propellant. However, it is known to the expert that the separation and purification of mixtures or certain components thereof by fractional distillation is only feasible if the distillation column is in equilibrium. Disturbances of the equilibrium caused by irregularities, operational changes, e.g. changes of the load, of start-up and shut-down procedures, or fluctuations of the amount of impurities entrained will result in insufficient purification of the dimethyl ether which will then be unfit for use as a propellant.

Mostly the odorants are still determined empirically. Direct sensory evaluations are made by an experienced team. For instance, a group of 150 people determined that the odour nuisance threshold for $H_2S$ is 45 $\mu g/m^3$ (cf. publications by 'Landesanstalt für Immissionsschutz des Landes Nordrhein-Westfalen', no. 49, 1979, p. 77).

In those cases where the odour nuisance can be measured by instruments the threshold values may also be determined by gas chromatography, specific conductivity, photometry or fluorescence (see 'Erdoel und Rohle, Erdgas, Petrochemie', vol. 32, no. 2, February 1975, p. 86).

The odour evaluations referred to in the present application were made sensorially.

Therefore, it was the object to remove the impurities from dimethyl ether which is particularly intended for propellant applications such that the dimethyl ether is largely odourless.

According to this invention, the problem was solved by treating the methanol feed, prior to charging it to the synthesis section for producing dimethyl ether, and/or the dimethyl ether product stream with acidic ion exchangers.

It was surprisingly found that odourless dimethyl ether can be obtained even under the problematic conditions mentioned hereinabove if the methanol feed, prior to charging it to the dimethyl ether synthesis, and/or the contaminated dimethyl ether product stream is/are treated with acidic ion exchangers.

Preferred materials are cationic exchangers based on cross-linked styrene polymerizates. Also suitable are acidic or acid-treated zeolites which the methanol feed for producing dimethyl ether or the contaminated dimethyl ether product stream is passed over.

The figures attached hereto illustrate embodiments of the present invention. They are described in the following. Depicted in the figures are the following process schemas:

FIG. 1 is a diagrammatic elevational view illustrating an ion exchanger vessel for treating the contaminated dimethyl ether, installed in the pertinent side drain of the distillation column or above and below this side drain.

FIG. 2 is a diagrammatic elevational view illustrating an ion exchanger vessel for treating the dimethyl ether product stream, installed in the product stream feed line to the distillation column.

FIG. 3 is a diagrammatic elevational view illustrating an ion exchanger vessel for treating the pure dimethyl ether, installed in the pertinent side drain of the distillation column.

FIG. 4 is a diagrammatic elevational view illustrating an ion exchanger vessel for treating the methanol feed, installed in the feed line to the synthesis reactor.

Although, as already mentioned hereinabove, the pure methanol used for the production of dimethyl ether contains lots of impurities which, after production of the crude dimethyl ether, are either chemically unchanged or, as a result of their contact with the dehydration catalyst, have undergone chemical changes, and although the quantities of impurities are such that they are mostly undetectable by customary analytical methods, the applicant has surprisingly found that by passing the 'pure methanol' or the dimethyl ether fractions over acidic ion exchangers odourless dimethyl ether is obtained even in those cases where the dimethyl ether distillation column is not in equilibrium. Consequently, it is sufficient to eliminate the basic components from the great number of impurities with their different chemical structures in order that an on-specs product is obtained, whichever operating conditions are chosen. By such treatment, however, additional reactions may take place on the acidic materials, e.g. formation of esters, amides or other compounds. Furthermore, in principle it is sufficient for the process according to the invention to use only one dimethyl ether distillation column instead of two (as in EP 0 124 078) with fewer plates, than required by that process. It is thus possible to produce odourless dimethyl ether with lower investment in a more economical way. Another positive aspect is that the reflux ratio in the distillation column producing the pure dimethyl ether can be reduced in comparison with a process without acidic ion exchanger treatment.

In principle, any commercially available acidic ion exchanger is suitable, but with respect to the process according to FIG. 3 it has to be observed that the ion exchanger of choice must be completely insoluble in dimethyl ether in order not to contaminate the purified dimethyl ether with dissolved ion exchanger. For example, the following ion exchangers may be used: Lewatit ® types, such as Lewatit S 100 (capacity 1–1.2 val/liter), Lewatit SP 112 (capacity 0.8–1 val/liter), Lewatit SP 120 (capacity 0.6–0.8 val/liter), or Amberlyst ® types, e.g. Amberlyst 15 (capacity approx. 1 val/liter), or any other type known in the art.

In the process according to FIGS. 1, 2 and 4 complete insolubility of the acidic ion exchangers is advantageous, but not imperative.

Preferably, the ion exchanger should be solid and arranged as a fixed bed in the vessel. The arrangement of the ion exchanger or any other solid acidic material is well known in the art.

Also two or more vessels holding the acidic ion exchanger can be connected, preferably in parallel. Such connections are also known in the art.

Using the figures attached hereto, the process according to the invention is described in detail.

In FIG. 1 the ion exchanger in vessel 1 is arranged as a fixed bed. A fraction of the pure dimethyl ether (fraction 1) is withdrawn from the distillation column (10) through line 4. A fraction of contaminated dimethyl ether (fraction 2) is withdrawn through line 2 or 3. The stream from lines 3 or 2 is returned through vessel 1 to the distillation column. This stream can also be passed over the ion exchanger from below. The ion exchanger of choice was a strongly acidic cation exchange resin with sulfuric acid groups marketed by Bayer under the trade name Lewatit SP 112.

It is expedient to withdraw (through line 4) the ether stream to be purified by ion exchanger treatment from a plate closely located below or above the plate from which fraction 2 is withdrawn (through line 3) because the concentration of impurities is relatively high in this region. Preferably, the stream to be purified is withdrawn from the same plate from which fraction 2 is withdrawn. If the same quantities are withdrawn through lines 3 and 4 and, after removal of 1–2% of the contaminated dimethyl ether through line 3a as fraction 2, the remainder is recycled via the ion exchanger, the number of plates between line 6 and line 4 can be reduced by approx. 60%. Line 6 is the crude dimethyl ether feed line, 5 is the overhead vapor line at the top of the column, and 8 is the discharge line for those products with a lower boiling point than dimethyl ether. Numeral 7 designates the reboiler; and 9, the bottom discharge line.

Odourless dimethyl ether was produced with 2,000 kgs of acidic ion exchanger for a pure dimethyl ether output of 10 cubic meters per hour during 8,000 hours (1 year) without reactivation of the ion exchanger. Although irregularities occurred in the load, start-up and shut-down procedures of the distillation column, pure, odourless dimethyl ether of consistent quality could be collected in a single storage tank. The same applies to the modes of operation described in the following.

In FIG. 2 the ion exchanger vessel (1) is placed in the crude dimethyl ether feed line (6). If more vessels are used, at least one is installed in line 6. The ion exchanger of choice was a strongly acidic cation exchange resin with sulfuric acid groups on macroporous cross-linked polystyrene marketed by Rohm & Haas under the trade name Amberlyst 15.

10 is the distillation column, 7 is the reboiler, 9 is the bottom discharge line, 5 is the overhead vapor line, and 8 is the light-ends withdrawal line.

Pure dimethyl ether is withdrawn through line 4. A contaminated fraction is removed through line 3.

Odourless dimethyl ether was produced with 4,000 kgs of acidic ion exchanger for a pure dimethyl ether output of 10 cubic meters per hour during 8,000 hours (1 year) without reactivation of the ion exchanger. Despite irregularities in the load, start-up and shut-down procedures odourless dimethyl ether was obtained. The quantity withdrawn through line 3 could be reduced to 0.1–0.2 weight percent of the crude dimethyl ether feed.

FIG. 3 shows the installation of the ion exchanger vessel (1) in line 4 through which pure dimethyl ether is withdrawn. The ion exchanger of choice was Lewatit SP 120.

The descriptions of the other apparatuses and lines are the same as in FIG. 2.

A trial run showed that odourless dimethyl ether was obtained with 200 kgs of acidic ion exchanger for a pure dimethyl ether output of 10 cubic meters per hour during 8,000 hours (1 year) without reactivation of the ion exchanger.

With 2,000 kgs of acidic ion exchanger the quantity withdrawn through line 3 could be reduced to 0.1–0.2 weight percent of the crude dimethyl ether feed, the yield of pure dimethyl ether thus being improved.

In FIG. 4 the ion exchanger vessel (1) is installed in line 11 through which pure methanol is fed to the dimethyl ether synthesis reactor (12). Crude dimethyl ether is withdrawn through line 13.

The ion exchanger of choice was Lewatit S 100.

Odourless dimethyl ether was obtained with 4,200 kgs of acidic ion exchanger and a pure methanol throughput of 10 cubic meters per hour during 8,000 hours (1 year) without reactivation of the ion exchanger.

Although the ion exchanger quantity has to be increased in comparison with the processes according to FIGS. 1 and 3, an odourless product is obtained in this case, too. The quantity removed through line 3 could be reduced as in the processes according to FIGS. 2 and 3.

In principle, an acidic ion exchanger bed can also be installed in the gas feed line to the methanol synthesis reactor, i.e. one step earlier than in the process according to FIG. 4.

The example described hereinabove make clear that the process according to the invention offers significant technical and economic advantages.

I claim:

1. In a process for producing odorless dimethyl ether by catalytic dehydration of methanol in a catalytic reaction zone and subsequent purification of the resultant crude dimethyl ether product stream by distillation in a separate distillation zone, the improvement which comprises treating the dimethyl ether reaction product from the catalytic reaction zone with an acidic ion exchange resin.

2. A process in accordance with claim 1 wherein the crude dimethyl ether product from the catalytic reaction zone is treated with an acidic ion exchange resin prior to purification by distillation.

3. A process in accordance with claim 1 wherein the dimethyl ether product from the catalytic reaction zone is treated with an acidic ion exchange resin during or after purification by distillation.

4. A process for producing odorless dimethyl ether by dehydration of methanol and subsequent purification of the resultant crude dimethyl ether product stream by distillation in a distillation column wherein during the distillation a contaminated dimethyl ether fraction is withdrawn from the distillation column, at least part of said fraction is treated with an acidic ion exchanger, and the greater part of the resultant treated fraction is returned to the column.

5. A process according to claim 4 wherein contaminated dimethyl ether in an amount in the range of 1 to 2 percent of the contaminated dimethyl ether fraction treated is discarded.

* * * * *